(12) United States Patent
Persson

(10) Patent No.: US 9,233,220 B2
(45) Date of Patent: Jan. 12, 2016

(54) PLASTER FOR TRACHEOSTOMA VALVES

(75) Inventor: Jan-Ove Persson, Höör (SE)

(73) Assignee: Atos Medical AB (SE)

( * ) Notice: Subject to any disclaimer, the term of this patent is extended or adjusted under 35 U.S.C. 154(b) by 692 days.

(21) Appl. No.: 11/012,299

(22) Filed: Dec. 16, 2004

(65) Prior Publication Data

US 2010/0258135 A1    Oct. 14, 2010

Related U.S. Application Data

(63) Continuation of application No. PCT/SE03/00840, filed on May 23, 2003.

(51) Int. Cl.
*A61M 16/04* (2006.01)

(52) U.S. Cl.
CPC .......... *A61M 16/047* (2013.01); *A61M 16/0468* (2013.01); *Y10T 156/10* (2015.01)

(58) Field of Classification Search
CPC .......... A61M 16/047; A61M 16/0472; A61M 2025/0233; A61M 2025/0923; A61F 13/02–13/0266
USPC .......... 128/207.14–207.18, 207.29; 604/339, 604/332, 338, 341; 623/9; 602/52, 54, 602/41–43, 48, 58
See application file for complete search history.

(56) References Cited

U.S. PATENT DOCUMENTS

| | | | | |
|---|---|---|---|---|
| 3,920,009 A | * | 11/1975 | Olsen | 128/201.13 |
| 4,318,406 A | * | 3/1982 | McLeod | 604/333 |
| 4,325,366 A | * | 4/1982 | Tabor | 128/207.16 |
| 4,518,388 A | * | 5/1985 | Jensen | 604/332 |
| 4,582,058 A | * | 4/1986 | Depel et al. | 128/207.17 |
| 4,645,556 A | * | 2/1987 | Waugh et al. | 156/242 |
| 4,846,820 A | * | 7/1989 | Jensen | 604/339 |
| 4,858,604 A | | 8/1989 | Konishi | |
| 4,917,112 A | * | 4/1990 | Kalt | 602/58 |
| 5,035,687 A | * | 7/1991 | Sandbank | 604/180 |
| D345,418 S | * | 3/1994 | Fenton | D24/129 |
| 5,666,950 A | * | 9/1997 | Smith | 128/207.14 |
| 5,718,696 A | * | 2/1998 | Kollerup | 604/339 |
| 5,730,735 A | * | 3/1998 | Holmberg et al. | 604/338 |
| 5,738,095 A | * | 4/1998 | Persson | 128/207.14 |
| 5,773,022 A | * | 6/1998 | Nyqvist-Mayer et al. | 424/443 |
| 5,868,132 A | * | 2/1999 | Winthrop et al. | 128/207.14 |
| 5,916,652 A | * | 6/1999 | Miner et al. | 428/41.8 |
| 6,051,249 A | | 4/2000 | Samuelsen | |

(Continued)

FOREIGN PATENT DOCUMENTS

| | | |
|---|---|---|
| EP | 0078685 | 5/1983 |
| EP | 0800804 | 10/1997 |

(Continued)

*Primary Examiner* — Steven Douglas
*Assistant Examiner* — LaToya M Louis
(74) *Attorney, Agent, or Firm* — Fishman Stewart Yamaguchi PLLC

(57) ABSTRACT

A plaster for attaching a trachestoma valve in connection with a traceostoma on a person's neck. The plaster comprises a socket and an annular flange, communicating with a central opening of the flange which is connected with a single-coated adhesive tape, which extends radially beyond the edge of the flange. The connection includes a first annular joint at or inwardly of the outer periphery of the flange, and a second annular joint located between the outer periphery of the flange and the inner periphery of the flange spaced radially from the first annular joint. A protecting liner covers the adhesive on the tape.

12 Claims, 4 Drawing Sheets

(56) References Cited

U.S. PATENT DOCUMENTS

| | | | |
|---|---|---|---|
| 6,790,200 B2* | 9/2004 | Fenton | 604/338 |
| 7,025,784 B1* | 4/2006 | Blom et al. | 623/9 |
| 7,374,626 B2* | 5/2008 | Van Der Leden | 156/73.1 |
| 2001/0020156 A1* | 9/2001 | Whiteside | 604/342 |
| 2003/0171737 A1* | 9/2003 | Leise et al. | 604/540 |
| 2003/0219469 A1* | 11/2003 | Johnson et al. | 424/445 |
| 2004/0106908 A1* | 6/2004 | Leise et al. | 604/332 |

FOREIGN PATENT DOCUMENTS

| | | |
|---|---|---|
| EP | 0927549 | 7/1999 |
| WO | WO 9724987 | 7/1997 |

* cited by examiner

PLASTER FOR TRACHEOSTOMA VALVES

FIELD OF THE INVENTION

The present invention relates to a plaster for attaching a tracheostoma valve or the like to a persons neck in connection with a tracheostoma, comprising a socket open at both ends thereof for mounting the valve or the like to the plaster, an annular flange integrally connected with a proximal end of the socket at an inner periphery of the flange concentrically surrounding said end, the flange being angled or curved towards the wall of the socket, an annular tape attached to a proximal side of the flange and covering said proximal side, and an adhesive on a proximal side of said tape.

A plaster of this kind is flangelosed in EP-A1-0 078 685.

BACKGROUND OF THE INVENTION

Due to disease, often cancer, it may be necessary to remove the larynx by surgery (laryngectomy). By removal of the larynx several important functions are lost. The epiglottis and the closing function thereof is lost, and therefore an opening into trachea, a tracheostoma, has to be provided in the neck of the patient in order to create a direct connection with trachea. The tracheostoma is sometimes lowered (depressed) in relation to the surface of the patient's neck around the stoma and may have an irregular form because it is often necessary to remove tissue around the stoma.

The vocal cords and thus the ability to speak are also lost. In order to re-create a kind of speech a fistula is formed by surgery between oesophagus and trachea, and a voice prosthesis which is a one-way valve (U.S. Pat. No. 5,578,083) is placed therein. By means of a finger or a tracheostoma valve the tracheostoma can be closed off in order to prevent air from going out through the tracheostoma, air being pressed from the lungs to oesophagus through the voice prosthesis whereby the mucosa of oesophagus is starting to vibrate and it is possible to speak (U.S. Pat. No. 4,325,366).

It is also known to connect some kind of heat and moisture exchanger to the tracheostoma. Therefore, the expression "tracheostoma valve" as used in the present description is meant to include any other appliance connected to the tracheostoma.

Irrespectively of the kind of appliance that is connected to the tracheostoma, the most common way to accomplish said connection is by means of an annular flange flange attached to the patient's neck by means of an adhesive. However, there is on the market also a disposable plaster for attaching tracheostoma valves to the neck, and this plaster is formed of a single-coated tape fixed to a flange. The flange forms a socket and a plane flange fixed to the tape. The plaster has a generally plane surface to be attached to the skin surrounding the tracheostoma. This type of plaster causes problems regarding tension and incomplete contact with the skin close to the tracheostoma due to the fact that the stoma normally is lowered or depressed.

Further prior art means for attachment to a patient's neck in connection with a tracheostoma includes an annular flange and a socket integral with the flange and projecting from one side thereof at an angle to the axis of the socket. The tracheostoma valve is exchangeably received in the socket. The flange is made of plasticized PVC. A double-coated tape is attached to the flange on the other side thereof as means for attaching the flange against the skin surrounding the tracheostoma. The tape must not extend beyond the edge of the flange, as any exposed adhesive of the tape will attract dirt and dust discolouring the tape. The flange is to be reused. Thus, when the tape is to be replaced the patient first has to remove the double-coated tape from the flange, clean the flange with a solvent, let the flange dry, and then apply a new double-coated tape to the flange. This procedure is repeated at least once a day.

Though the products of the above type work well in many respects, there are still some problems. The known products are normally of a type to be re-used, which means that cumbersome cleaning by means of unhealthy solvents has to be effected. Often the patient is elderly and will find problems in performing these steps. In order that the tape shall adhere to the flange this is made of plasticized poly-vinyl chloride (PVC). This plastic is known to cause health problems and accordingly should be avoided. The tape is fixed to the whole area of the flange, which means that it relatively easy may come loose from the skin due to the fact that a large force is concentrated to the tape edge adjacent the tracheostoma. When the tracheostoma valve is used during speaking and coughing or is to be removed, the socket is exposed to large axial forces, putting the tape edge adjacent the socket under tension. As the flange is relatively small and the adhesive tape does not extend beyond it or at least not far beyond it, it is difficult to have sufficient adherence on patients having a large and irregular tracheostoma. The flange is inclined but since the tracheostoma often is lowered or depressed and the skin around the tracheostoma often is relatively plane the inclined flange will cause surrounding skin to adapt an unnatural form and in this way creates tensions in the tissues and thus flangeomfort to the patient. Furthermore, there is an increased risk that the plaster will more easily loosen from the patient's neck.

SUMMARY OF THE INVENTION

One object of the present invention is to provide a plaster of the kind referred to herein having attachment means that follows the depressed or lowered tracheostoma and the relatively plane surrounding skin for optimal adherence without causing any tension or discomfort to the patient. The attachment means should also be able to take up much larger forces and not come loose as easily as prior art products. Furthermore, the plaster should be less cumbersome to handle for the patient.

The above objects are attained according to the present invention by a plaster of the kind referred to which according to claim 1 is characterized in that the annular tape is a single coated adhesive tape attached to the flange by a first annular joint at or inwardly of the outer periphery of the flange and extends radially beyond the edge of the flange, and that the annular tape is attached to the flange by a second annular joint located between said outer periphery of the flange and said inner periphery of the flange spaced radially from said first annular joint, a protecting liner covering the adhesive on the tape.

A further object of the present invention is to provide a plaster for connection to the tracheostoma which is of disposable type so that there is no need for the patient to perform the cumbersome and health jeopardising steps of changing the double-coated adhesive tape, which by many patients is felt as a major problem.

A still further object is to provide a plaster which can cover also big and irregular tracheostomas.

Another object is to make the plaster of biocompatible and environment friendly materials, reducing risks for both patient and environment.

Further advantageous features of the invention are defined in the dependent claims.

In order to adapt the plaster to different types of tracheostomas the design of the adhesive tape may be adjusted as to form and size without the flange being a limiting element as is the case with prior art devices.

Further objects and advantages of the present invention will be obvious to a person skilled in the art when reading the following detailed description of illustrative embodiments of the invention.

BRIEF DESCRIPTION OF THE DRAWINGS

In the accompanying drawings.

DETAILED DESCRIPTION OF PREFERRED EMBODIMENTS

Figure 1:
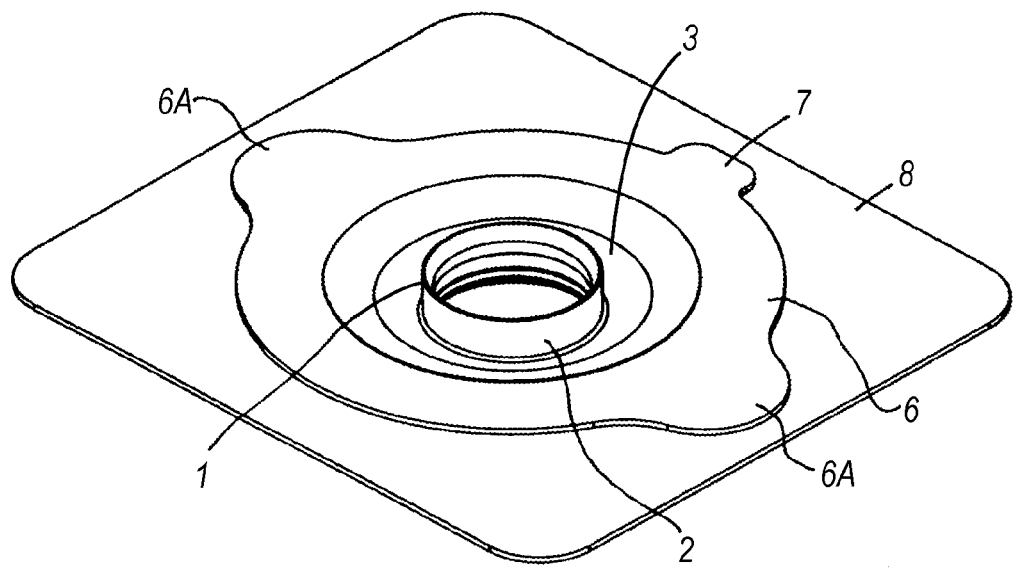
FIG. 1 is a perspective view of a plaster for tracheostoma valves or the like according to a first embodiment of the invention as seen from the distal side thereof.

The plaster according to the present invention comprises a first flange or central, annular flange 1 (hereinafter "flange 1"), which forms a central socket 2 and a second flange or flange 3 thereinafter "flange 3") concentrically surrounding socket 2. Thus, socket 2 forms a central opening of flange 1. In the embodiments of FIGS. 1 to 5, flange 3 is inclined at an angle 4 in relation to the central axis 9 of socket 2. The angle 4 may vary but is preferably between 30° and 80° and more preferably between 50° and 70°. Due to the angle 4 of flange 3 a base plane 11 perpendicular to axis 9 and including the area where socket 2 and flange 3 are joined, is placed at a distance 10 from a top plane 12 perpendicular to axis 9 and located at the highest or relatively plane level of the plaster. Distance 10 between base plane 11 and top plane 12 normally is between 2and 15mm, and preferably between 3and 10mm.

The annular flange 1 is preferably made of low density polyethylene, which is a very biocompatible and soft polymer. The flange may also be made of other relatively soft polymers.

A single-coated adhesive tape 6 which has adhesive on one side only, as distinct from a double-coated adhesive tape which has adhesive on both sides thereof is attached to flange 3. Tape 6 is preferably of a medical grade and extends beyond the edge of flange 3 of the annular flange 1 and has a generally plane form outside the flange. Tape 6 extends along flange 3 of flange 1 close to the edge of socket 2, and at the outer periphery it forms two diametrically opposite enlargements 6A which increase the surface to be attached to the skin around the tracheostoma by the adhesive tape. In the manufacture of the plaster the adhesive of tape 6 is covered by some kind of liner or backing 8 which should be removed before the tape is attached to the patient. Tape 6 forms a flap 7, which is not covered by adhesive. This flap 7 facilitates removal of liner 8 from tape 6. Tape 6 is preferably made of polyethylene but may also be made of other biocompatible materials.

Flange 1 and the adhesive tape 6 are fixed to each other by means of two annular welds 5A and 5B extending around flange 3 of flange 1 concentrically with socket 2. One weld 5A is placed adjacent the outer edge of flange 1 and the other weld 5B at a relatively short radial distance inwardly of the edge radially spaced from socket 2. Preferably the radial distance between the innermost weld 5B and the inside surface of socket 2 is at least 2 mm. The welds may be formed by means of heat or ultrasonic welding e.g. by using impulse welding or a continuously heated welding head. As there is a distance between socket 2 and welds 5A, 5B axial forces on socket 2 will not put the tape edge under large tension, which is the case in the prior art products where there is no such distance.

Figure 2:
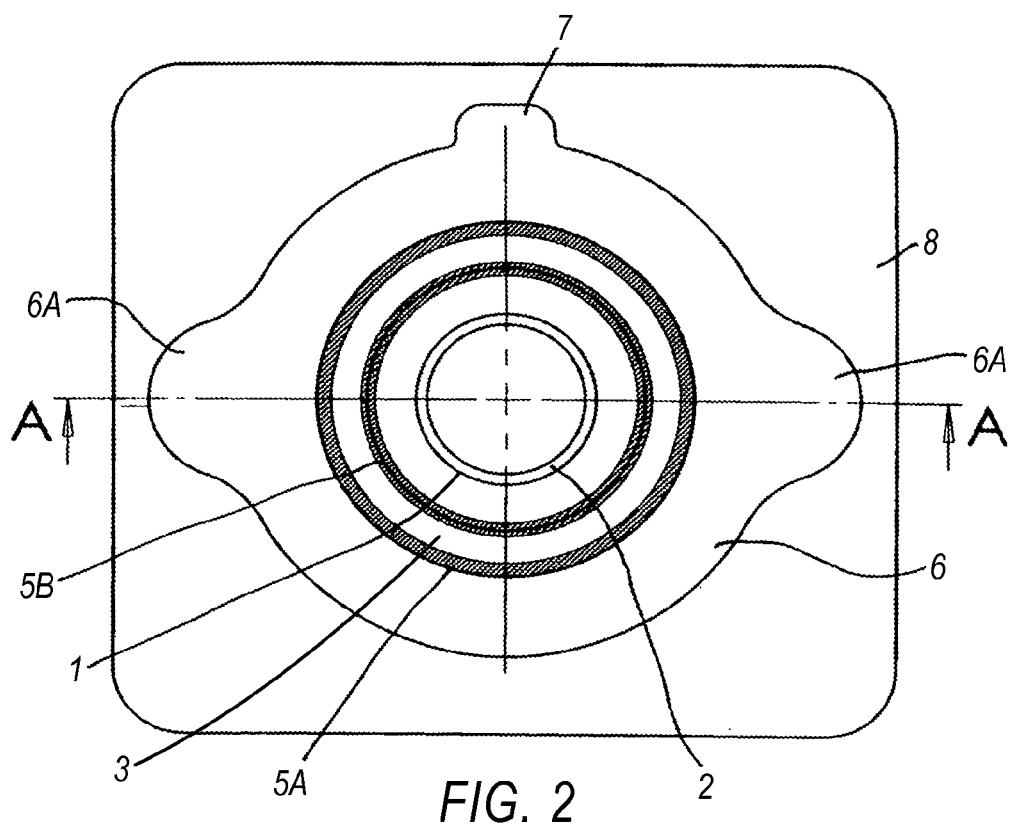
FIG. 2 is a plan view of the distal side of the plaster of FIG. 1.
Figure 3:
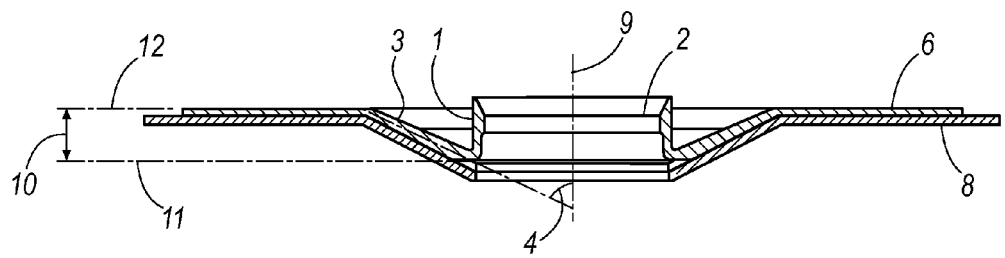
FIG. 3 is a cross sectional view of the plaster of FIGS. 1 and 2, taken along line A-A of FIG. 2.
Figure 4:
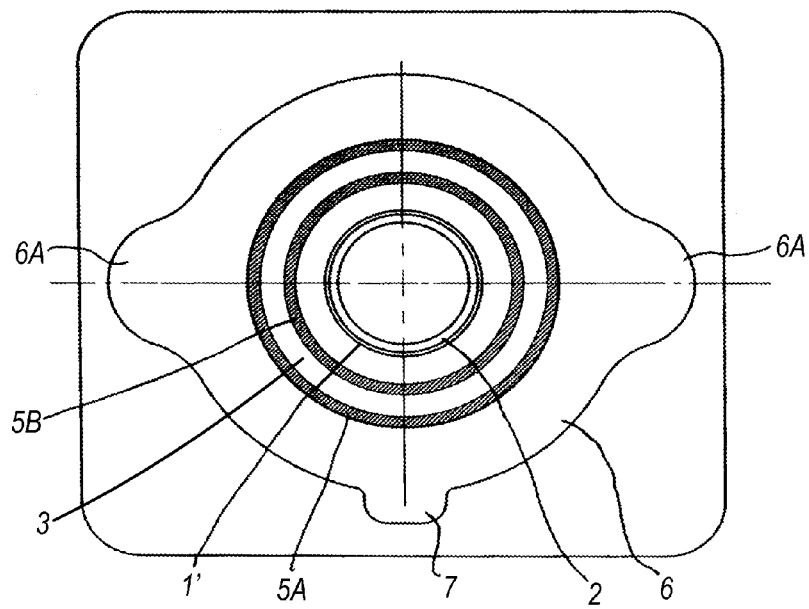
FIG. 4 is a plan view of a second embodiment of a plaster for tracheostoma valves or the like as seen from the distal side.
Figure 5:
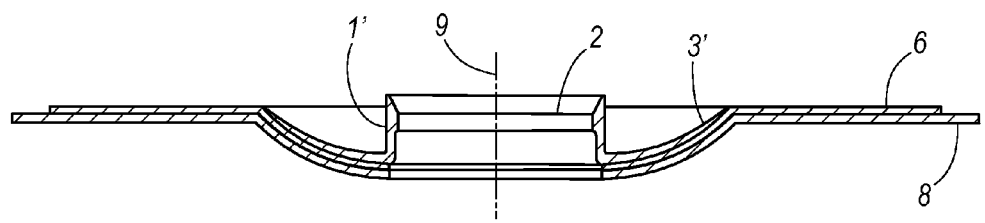
FIG. 5 is a cross sectional view as in FIG. 3 of the plaster of FIG. 4.

The embodiment of FIGS. 4 and 5 differs from the embodiment of FIGS. 1 to 3 regarding the form of the flange 3' of the flange 1'. Flange 3' has a curvature as seen in cross section. The curvature of flange 3' may vary. In the same way as in the previous embodiment by the curvature of flange 3' the base plane 11 is placed at a distance 10 from the top plane 12. Said distance 10 between the two planes 11, 12 is normally between 2 and 15 mm, and most preferably between 3 and 10 mm.

In the embodiments shown flange 3 of flange 1 of FIGS. 1 to 3 is generally conical while flange 3' of flange 1' of FIGS. 4 and 5 has a curvature. The person skilled in the art realises that the flange may have any curvature as long as it has a general inclination in relation to the central axis 9 of socket 2. As stated above the purpose of the general inclination is to adapt the plaster to the form of the tracheostoma which normally is lowered or depressed in relation to the surrounding skin.

Conventional paper liners cannot be used with plasters having a flange 1, 1' with an inclined or curved flange 3, 3'. Liner 8 most follow the form of the plaster, other-wise the adhesive will dry at areas with no contact between plaster and liner. Thus, it should be possible to form the liner 8 so as to bring the shape thereof into agreement with the shape of the adhesive tape 6, either by cold forming or by thermo forming. The forming of the liner 8 and tape 6 may be done by means of a stamp or by vacuum forming, or blow moulding before, during, or after the fixation of the tape 6 to the flange 1, 1'. According to a presently used method liner 8 and tape 6 are formed by cold forming before securing tape 6 to flange 1, 1'. However, it is always necessary to adapt the form of liner 8 to the form of the plaster.

When the plaster for the tracheostoma valve is to be applied, liner 8 is first removed. Tape 6 is then applied to the skin surrounding the stoma. The plaster is placed in a position where the central socket 2 is aligned with the stoma. Then, the tracheostoma valve is attached to the socket 2. It is the lower side of the plaster as seen in FIGS. 2 and 5 which is to be applied against the skin of the patient. When the plaster is to be replaced the above procedure is reversed, i.e. first the valve is removed, then the plaster, including the annular flange 1, is removed and discarded. Finally a new plaster is applied as stated above. Thus, the plaster is not to be re-used, avoiding the previous problems with cleaning of the flange.

Figure 6:
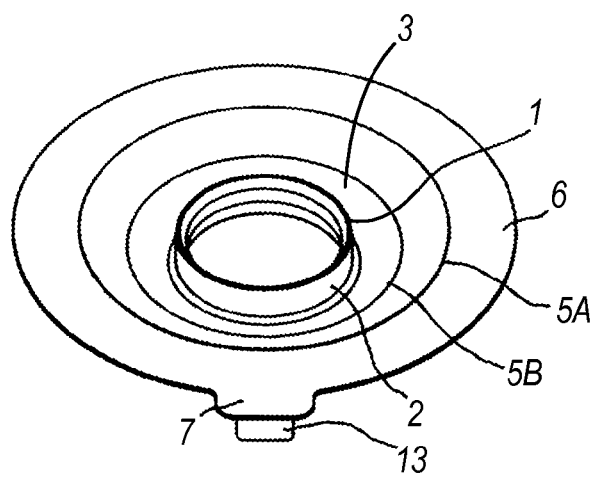
FIG. 6 is a perspective view as seen from the distal side of a plaster according to a third embodiment of the invention.
Figure 7:
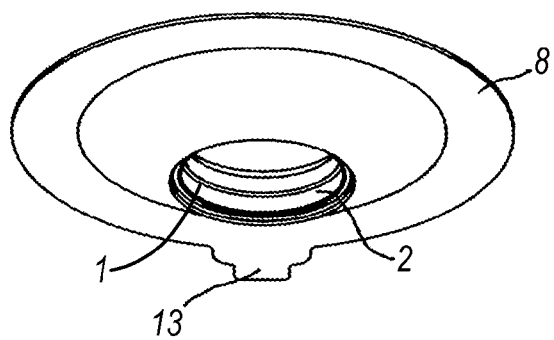
FIG. 7 is a perspective view of the plaster in FIG. 6 as seen from the proximal side thereof.

The shape of the tape 6 can be varied in many ways. In FIGS. 6 and 7 the tape and the liner are circular and are substantially congruent. There are no enlargements as those shown in FIGS. 1, 2 and 4. Liner 8 forms a flap 13 which projects from flap 7 on tape 6. The tape and the liner can easily be gripped at the flaps when it is desired to remove the liner from the adhesive surface of the tape.

Figure 8:
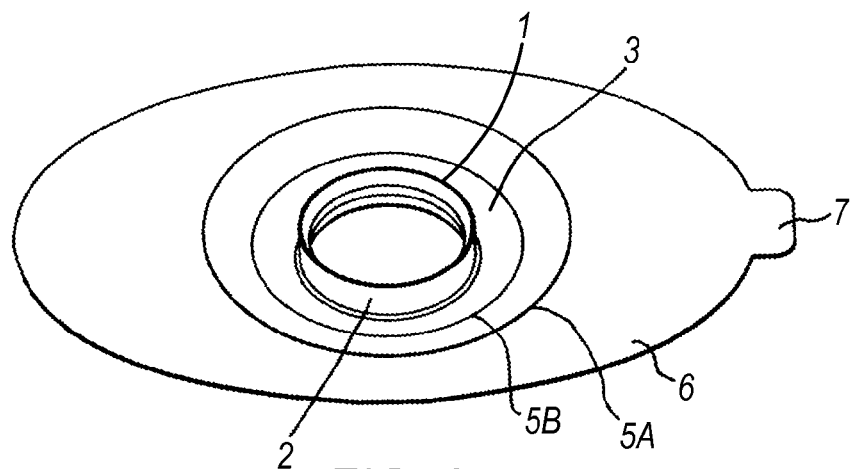
FIG. 8 is a perspective view of a fourth embodiment of the plaster of the invention as seen from the distal side thereof.

In FIG. 8 tape 6 and liner 8 are oval. Flap 7 (and flap 13) are located at one short side but can as well be located at one long side of tape 6 and liner 8, respectively, or anywhere on the periphery of the tape and the liner.

Figure 9:
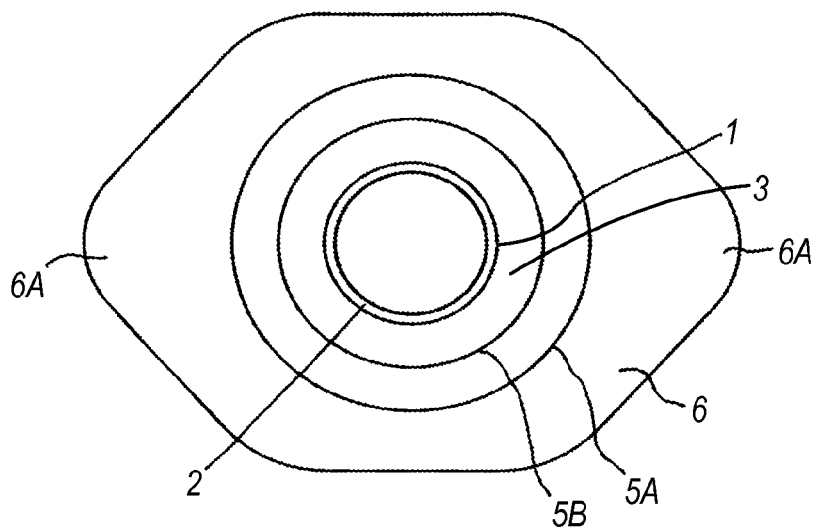
FIG. 9 is a plan view of a fifth embodiment of the plaster of the invention as seen from the distal side thereof.
Figure 10:
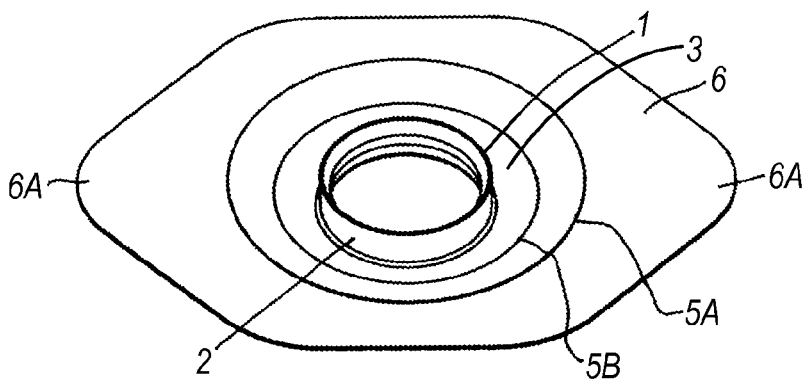
FIG. 10 is a perspective view of the plaster in FIG. 9 as seen from the distal side thereof.
Figure 11:
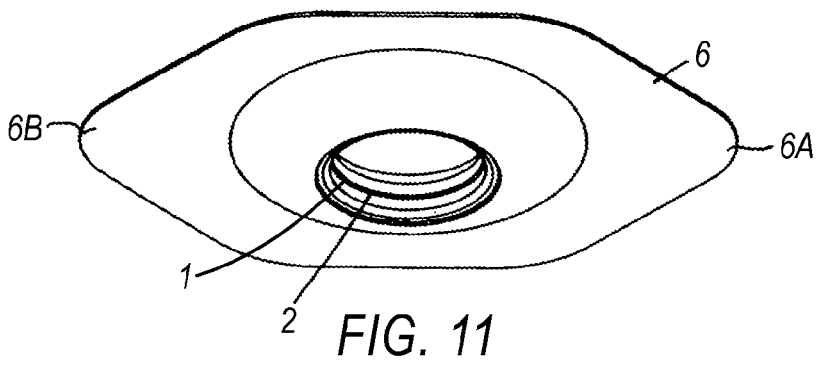
FIG. 11 is a perspective view of the plaster in FIG. 9 as seen from the proximal side thereof.

FIGS. 9 to 11 show a still further shape of tape 6 and liner 8. The shape is basely a rectangular shape with enlargements 6A at two opposite sides.

The person skilled in the art realizes that the different parts may be adapted to the actual patient. Thus, the thickness and material of the adhesive tape may vary, e.g. due to the sensitivity of the patient's skin or the like. The extension of the tape outside the flange may also vary. Also the size and thickness of the flange may be varied.

The invention claimed is:

1. A plaster for attaching a tracheostoma valve on a person's neck in connection with a tracheostoma, having a proximal side and a distal side and comprising:
    an annular first flange forming a socket open at both ends thereof for mounting the valve to the plaster;
    an annular second flange having an inner periphery integrally connected with a proximal end of the annular first flange within a base plane that is disposed perpendicular to an axis of the socket, and the inner periphery of the second flange concentrically surrounds the proximal end of the annular first flange, the second flange being curved in cross section towards a cylindrical wall formed by the annular first flange;
    an annular tape attached to a proximal side of the second flange and covering the proximal side, such that the annular tape is disposed between the proximal side of the second flange and an area surrounding the tracheostoma, and an adhesive on a proximal side of the annular tape, wherein the annular tape is a single coated adhesive tape attached to the second flange by a first annular joint at or inwardly of an outer periphery of the second flange, and extends radially beyond an edge of the second flange, and the annular tape is attached to the second flange by a second annular joint located between the outer periphery of the second flange and the inner periphery of the second flange spaced radially inwardly from the first annular joint, the annular tape extending radially beyond the first annular joint; and a protecting liner covering the adhesive on the annular tape;
    wherein the annular tape is a single sided adhesive tape having one side with an adhesive and another side without the adhesive;
    wherein a portion of the side of the annular tape without the adhesive extends radially beyond the second flange;
    wherein the second annular joint is spaced concentrically outward from the socket, and the first annular joint is spaced concentrically outward from the second annular joint, so as to reduce axial tension on an inner edge of the tape when an axial force is applied to the socket;
    wherein a highest end of the plaster is disposed in a top plane, and a distance between the top plane and the base plane is between 2 millimeters and 15 millimeters.

2. The plaster of claim 1, wherein the annular tape extends from adjacent the socket beyond an outer edge of the second flange and is mainly planar in an area outside an area of the second flange.

3. The plaster of claim 1, wherein the protective liner covering the adhesive of the annular tape is imparted the same form as the annular tape.

4. The plaster of claim 3, wherein the annular tape and the protective liner are formed by one of cold and thermo pressing.

5. The plaster of claim 1, wherein the annular tape extends radially beyond the first annular joint by at least a radial distance equivalent to a width of the first annular joint.

6. The plaster of claim 1, wherein the side of the annular tape without the adhesive has uninterrupted contact with the proximal side of the second flange.

7. The plaster of claim 1, wherein the second annular flange concentrically surrounds the socket, and the annular tape extends beyond an edge of the second flange.

8. The plaster of claim 1, wherein the annular tape includes a pair of diametrically opposed enlargements.

9. The plaster of claim 1, wherein the annular tape includes a flap without any adhesive to facilitate removal of the liner from the tape.

10. The plaster of claim 1, wherein the annular first flange is a cylindrical body having a constant inner diameter.

11. The plaster of claim 1, wherein the inner edge of the tape is disposed adjacent to the socket, and the inner edge of the tape is not welded to the socket, so as to reduce axial tension on the inner edge of the tape when an axial force is applied to the socket.

12. A plaster for attaching a tracheo stoma valve on a person's neck in connection with a tracheostoma, having a proximal side and a distal side and comprising:
    an annular first flange forming a socket open at both ends thereof for mounting the valve to the plaster;
    an annular second flange having an inner periphery integrally connected with a proximal end of the socket within a base plane that is disposed perpendicular to an axis of the socket, and the inner periphery of the second flange concentrically surrounds the proximal end, the second flange being curved in cross section towards a cylindrical wall of the socket;
    an annular tape attached to a proximal side of the second flange and covering the proximal side, such that the annular tape is disposed between the proximal side of the second flange and an area surrounding the tracheostoma, and an adhesive on a proximal side of the annular tape, wherein the annular tape is a single coated adhesive tape attached to the second flange by a first annular joint at or inwardly of an outer periphery of the second flange, and extends radially beyond an edge of the second flange, and the annular tape is attached to the second flange by a second annular joint located between the outer periphery of the second flange and the inner periphery of the second flange spaced radially inwardly from the first annular joint, the annular tape extending radially beyond the first annular joint; and a protecting liner covering the adhesive on the annular tape;
    wherein the annular tape is a single sided adhesive tape having one side with an adhesive and another side without the adhesive;
    wherein a portion of the side of the annular tape without the adhesive extends radially beyond the second flange;
    wherein the second annular joint is spaced concentrically outward from the socket, and the first annular joint is spaced concentrically outward from the second annular joint, so as to reduce axial tension on an inner edge of the tape when an axial force is applied to the socket;
    wherein a highest end of the plaster is disposed in a top plane, and
    wherein a distance between the top plane and the base plane is between 3 millimeters and 10 millimeters.

* * * * *